(12) United States Patent
Brothier et al.

(10) Patent No.: US 8,054,082 B2
(45) Date of Patent: Nov. 8, 2011

(54) DEVICE AND METHOD FOR COUPLED MEASUREMENTS FOR GLOBALLY AND CONTINUOUSLY TRACKING TRACES OF TARS PRESENT IN A GAS FLOW

(75) Inventors: Meryl Brothier, Aix en Provence (FR); Pierre Estubier, Manosque (FR); Julien Comte, Pontcharra (FR); Patrick Baussand, Uriage les Bains (FR); Johann Soyez, Aubagne (FR)

(73) Assignee: Commissariat a l'Energie Atomique, Paris (FR)

( * ) Notice: Subject to any disclaimer, the term of this patent is extended or adjusted under 35 U.S.C. 154(b) by 345 days.

(21) Appl. No.: 12/518,505

(22) PCT Filed: Dec. 28, 2007

(86) PCT No.: PCT/EP2007/064639
§ 371 (c)(1),
(2), (4) Date: Jun. 10, 2009

(87) PCT Pub. No.: WO2008/080987
PCT Pub. Date: Jul. 10, 2008

(65) Prior Publication Data
US 2010/0045300 A1 Feb. 25, 2010

(30) Foreign Application Priority Data

Dec. 28, 2006 (FR) .................................. 06 56004

(51) Int. Cl.
*G01N 27/62* (2006.01)
(52) U.S. Cl. .......... 324/468; 324/464; 73/23.2; 250/389

(58) Field of Classification Search .................. 324/468, 324/464; 72/23.2; 259/389
See application file for complete search history.

(56) References Cited

U.S. PATENT DOCUMENTS

| 5,415,025 A | 5/1995 | Bartman et al. |
| 5,703,360 A | 12/1997 | Fischer et al. |
| 6,225,633 B1 * | 5/2001 | Sun et al. ...................... 250/389 |
| 2002/0048818 A1 | 4/2002 | Sakairi et al. |

FOREIGN PATENT DOCUMENTS

| DE | 160 249 A3 | 5/1983 |
| DE | 1602 49 A1 | 5/1983 |
| DE | 198 32 411 A1 | 3/1999 |

(Continued)

OTHER PUBLICATIONS

Broutin et al; "Anticoking Coatings for High Temperature Petrochemical Reactors", Oil & Gas Science and Technoiogy-Rev, IFP, vol. 54 (1999) No. 3, pp. 375-385.

(Continued)

*Primary Examiner* — Vincent Q Nguyen
(74) *Attorney, Agent, or Firm* — Pearne & Gordon LLP

(57) ABSTRACT

The measurement is carried out by a device of two non-dissociable measurement chains resulting in a continuous measurement which is representative of the total concentration of tars (even as traces) of a hot gas. It involves coupling of methods including one, SPME/GC/MS/PID, which is discontinuous and a priori partial, the other, PID, which is continuous but difficult to interpret alone. It is based on on-line processing of the elements transmitted by each of the measurement methods used. A tar generator (28) allows calibration of the apparatuses and calculation of the different coefficients required.

22 Claims, 5 Drawing Sheets

FOREIGN PATENT DOCUMENTS

| | | |
|---|---|---|
| EP | 0 586 012 A2 | 3/1994 |
| EP | 1 102 004 A1 | 5/2001 |
| JP | 2005-274502 A | 10/2005 |
| WO | 03/054246 A1 | 7/2003 |
| WO | 2006/014555 A1 | 2/2006 |

OTHER PUBLICATIONS

Pindoria et al; "A two-stage fixed-bed reactor for direct hydrotreatment of volatiles from the hydropyrolysis of biomass: effect of catalyst temperature, pressure and catalyst ageing time on product characteristics", Fuel, vol. 77, No. 15; Dec. 1, 1998 pp. 1715-1726.

Xu et al; "Comparison of a Solvent-Free Tar Quantification Method to the International Energy Agency's Tar Managment Protocol", Energy & Fuels 2005, pp. 2509-2513.

Carpenter et al; "Quantitative Measurement of Biomass Gasifier Tars Using a Molecular-Beam Mass Spectrometer: Comparison with Traditional Impinger Sampling", Energy & Fuels 2007, No. 21, pp. 3036-3043.

Bain et al; "Evaluation of Catalyst Deactivation during Catalytic Steam Reforming of Biomass-Derived Syngas", Industrial and Engineering Chemistry Research, vol. 44, No, 21 Oct. 12, 2005 pp. 7945-7956.

French Search Report for FR 709590 dated Apr. 19, 2009.
French Search Report for FR 709589 dated Apr. 19, 2009.
International Search Report for PCT/EP2007/064639.
International Search Report for PCT/EP2007/064562.

* cited by examiner

DEVICE AND METHOD FOR COUPLED MEASUREMENTS FOR GLOBALLY AND CONTINUOUSLY TRACKING TRACES OF TARS PRESENT IN A GAS FLOW

TECHNICAL FIELD

The present invention relates to the field of techniques for analyzing and measuring pollutants in a gas flow.

More particularly, it relates to a device and a method for continuously measuring tars of a gas, these tars being able to be tar traces.

STATE OF THE PRIOR ART

One of the major problems encountered in vapo-gasification is to be able to continuously assess the quality of the generated gas in order to make sure that the latter complies with specifications required by its application (generation of electricity, of mechanical energy, of heat, synthesis of fuels or other chemical products or further formation of hydrogen).

Assessing the specifications of synthesis gas requires knowledge of the composition of the gas and therefore i.a. the concentration of the different pollutant species; these are sulfur-, nitrogen-, chlorine-containing compounds, alkaline metals, dusts and tars.

The presence of tars in gases derived from gasification poses many problems in the different targeted applications, such as for example deterioration of the blades of turbines or further the loss of activity of catalysts by inactivation, notably as regards metal and zeolite catalysts. Tars may pose other problems notably in pyrolysis or gasification reactors where under the action of heat, they give rise to a deposit of heavy hydrocarbon compounds, called coke, on the walls of the reactor; this phenomenon bearing the name of coking. As a result of this deposit, transfers of heat to the reactor are thereby reduced. Formation of coke also tends to increase pressure losses in the conduits and in the absence of corrective action ends with blocking the ducts.

There is therefore a real industrial need for having a device for a method for measuring tar traces which is both quantitative, continuous and on-line.

Moreover, tars, as byproducts of the heat degradation of organic material, are good indicators in terms of monitoring of vapo-gasification methods. Thus, continuous measurement of the concentration of tars or at the very least the tracking of the concentration of tracers, representative molecules of categories of tars, may be a diagnostic and control tool for gasification methods with view to real-time optimization of the parameters of the latter.

Now, the measurement of the content of tars, present as traces in the gas flow, is subject to many difficulties.

A first difficulty is related to the meaning of the generic term <<tar>> which differs according to the relevant field of application. Within the scope of atmospheric pollution, of metallurgy, of waste incineration, of cogeneration and production of synthetic fuels, by <<tar>> is generally designated the whole of the organic compounds having a molecular mass above that of benzene—i.e. 78 g/mol—but there is no official definition for this term, and the literature reports about thirty definitions for the word <<tar>>, the meaning of which is still today subject to discussions. As an indication, we may cite a few of these definitions: <<mixture of chemical compounds condensing on metal surfaces at room temperature>> or further <<the whole of the components having a boiling temperature above 150° C.>>.

Tars cover a wide spectrum of species (more than 2,000), the physico-chemical characteristics of which (polarity, volatility, molar mass, chemical affinity) vary over a large range of values, which makes it particularly difficult to obtain a measurement reporting the total tar content. Several classifications of these various compounds have been proposed today, as for example the classification of *Milne & Evans* (1998) which lists the different tars in three classes:

Class 1: primary species,
Class 2: secondary species,
Class 3: tertiary species.

The main components are polycyclic aromatic hydrocarbons (PAHs), volatile organic compounds (VOCs) and phenols.

There exist various techniques for measuring tars but the latter only partly meet the measurement needs.

For this purpose, it is desirable to have a device and a method which simultaneously fulfill the following functions:

carry out a measurement of tars present as traces (at concentrations of the order of mg/Nm$^3$ or even less) in a gas matrix;

carry out a quantitative measurement of the whole of the tars, regardless of their physical states. Indeed, in order to estimate the quality of the gas, it is absolutely necessary that the measurement should be representative of the total concentration of tars present in the gas flow to be characterized;

carry out a real-time measurement, i.e. the device should be capable of providing a measurement every minute, or at least the occurrence of a measurement has to be compatible with tracking which may be considered at continuous (of the order of one minute), including trace concentrations;

carry out an on-line measurement of the concentration of tars and at the very least conduct the measurement under temperature and pressure conditions as close as possible to those prevailing in a main conduit in which flows a synthetic gas to be analyzed. The question is of avoiding any notable modification of the tar concentration by a change in value of the temperature and pressure parameters. In the case of fuel synthesis by the Fischer-Tropsch process, the gas to be measured has a temperature of about 300° C.;

not perturb the industrial process for producing gas both upstream and downstream.

The methods proposed hitherto for determining the tar concentration of a gas are divided into four large families:

a first family which groups so-called << spectrometric methods >>, which consist in detecting and analyzing a spectrum. This is for example infrared, ultraviolet (UV) or luminescence spectrometry, LIBS (Laser-Induced Breakdown Spectroscopy) technique or mass spectrometry. The advantage of applying UV absorption which is very close to that of absorption in the infrared, is that steam does not interfere in the UV range. The latter is used for example for detecting polycyclic aromatic hydrocarbons in contaminated soils as mentioned in patent EP0446975 entitled <<Installation of the rapid analysis of tar components and method for such an analysis >>. Patent WO9833058, as for it, relates to a method for on-line analysis of polycyclic hydrocarbons by collecting the aerosols by means of a filter and by submitting the latter to excitation via UV radiation. Next, the question is of comparing the obtained spectral image with various spectra listed in a database. Another currently used technique in the continuous monitoring of combustion gases is FTIR (Fourier Transform Infra- Red) infrared spectrometry. Miscellaneous documents mention this technique, such as for example WO2006015660, WO03060480 and U.S. Pat. No. 5,984,998. The literature does not mention a possibility of measuring tars, the currently tracked products being CO, $CO_2$, $O_2$, $H_2$ and $H_2O$. In our case, the presence of steam in the synthesis gas is a source of perturbation in infrared absorption. The FTIR method is qualitative in the sense that it gives information on the nature and the proportion of atomic groups and that only asymmetrical molecules may be measured. Another limitation consists in the determination of mathematical models required for quantifying the measurement. Patent WO030227650 relates to the use of the LIBS (Laser-Induced Breakdown Spectroscopy) technique with view to detecting polycyclic aromatic hydrocarbons (PAHs) and mono-aromatics. This fast method is adapted to the monitoring of PAHs. The LIBS technique consists of vaporizing and ionizing the sampled species as a plasma by means of a laser. However it requires the use of a support on which are present the species to be analyzed. It therefore requires a sampling step and does not make possible a continuous and on-line measurement of the gas. Finally, mass spectrometry applied to the measurement of compounds, generating a large number of spectral interferences (as this is the case for organic compounds such as tars), can only be used for specific cases (as in the case discussed in patent 2002/0048818 based on the strong electronegativity of ions from ionization of dioxins because of the presence of hetero-atoms in the compounds to be quantified). Moreover, without any concentration step, this technique is not very suitable for quantifying traces, strictly speaking;

a second family which groups so-called <<gravimetric>> methods of which a division may be made depending on whether solvents are used or not. The large majority of the methods encountered in the literature involve at least one solvent. They use in a combined way the same physical principles which are: filtration (impaction), condensation, absorption by solvent and extraction (evaporation). Next the question is to evaluate the mass difference of the various elements (filters, cryogenic traps, . . . ) by weighing between the beginning and the end of the measurement. These methods, with an often complex and long experimental procedure, are exclusively suitable for a use in the laboratory. They require a significant sampling time (>30 min) in order to be able to detect low concentrations (less than 1 mg/$Nm^3$) and they do not allow continuous and on-line tracking of the tar content of a hot gas. The work originating from the European <<tar protocol>> project (ENK5 CT 2002-80648) is a reference in the field of analysis measurement of the tar content of gases from gasification processes. The last version (version 3.3) to date is entitled <<Guideline for Sampling and Analysis of Tar and Particles in Biomass Producer Gases>>. With this procedure it is possible to conduct both a quantitative and qualitative measurement of tars present in the gas state and in the solid state per sample. The measurement is conducted by isokinetic sampling for a range of temperatures from 0 to 900° C. and a pressure ranging from 0.6 to 60 bars and this for a tar concentration ranging from 1 to 300 mg/$Nm^3$. This protocol proves to be thus unsuitable for measuring tar traces (<1 mg/$Nm^3$). There exist a large number of procedures derived from this protocol which aim at simplifying the latter. Generally, gravimetric methods prove to be suitable for the measurement of so-called <<heavy>> tars (with more than 3 aromatic rings as regards polycyclic aromatic hydrocarbons, the so-called PAHs) but not very suitable for that of volatile organic compounds. As mentioned above, there also exist gravimetric methods which do not use any solvent such as the one developed by Iowa State University. In the document referenced as: Ming Xu, Robert C. Brown, Glenn Norton, and Jerod Smeenk, <<Comparison of a Solvent-Free Tar Quantification Method to the International Energy Agency's Tar Measurement Protocol>>, Center for Sustainable Environmental Technologies, Iowa State University, Energy & Fuels 2005, 19, 2509-2513, the authors propose a measurement, the principle of which consists of condensing the organic components in a Santoprene tube maintained at a temperature (105° C.) above that of boiling water. Santoprene is a material which was selected for its resistance towards the devolatilization phenomenon. The advantage of this method lies in its simplicity but it requires a sampling time of 60 minutes for a gas flow rate of 2 L/min in order to obtain a detection limit of the order mg/$Nm^3$. The obtained performances are very close to that of the <<tar protocol>> but with this method, it is only possible to measure so-called <<heavy>> tars. This is therefore a relatively long, partial and non-continuous method.

a third family which groups so-called <<electronic>> methods. We may cite as an example the measurement of organic compounds by means of FID (Flame Ionization Detector) detectors or PID (Photo Ionization Detector) detectors. The document referenced as: O. Moersch, H. Spliethoff, K. R. G Hein, <<Tar quantification with a new online analyzing method >>, Biomass and Bioenergy, Volume 18, 2000, pages 79-86, mentions a quasi-continuous method for determining tars by means of two flame ionization detectors (FIDs). With a first detector it is possible to determine the total amount of hydrocarbons and the second measurement determines the amount of non-condensable hydrocarbons. Both detectors are placed in different points of the same sampling conduit for the gas to be characterized and are separated by a filter which has the purpose of trapping the tars by impaction and condensation. One of the limits of the flame ionization technique is the perturbation of the measurement by combustible gases such as $CH_4$ and $H_2$, which is a real limitation insofar that synthesis gas is a mixture of CO and $H_2$ and that it also contains methane. Further, the response depends on the oxygen content of the gas to be measured. Finally, the measurement of organic compounds by flame ionization just like the measurement by photo-ionization, requires knowledge of the composition of the tars as well as of the response factors of various compounds in order to obtain a quantitative measurement of the total tars. Indeed, the intensity of the response depends on the given species, which therefore requires intervention of a correction coefficient. Photo-ionization, contrary to the flame ionization technique, is a non-destructive measurement method. Moreover, the presence of methane, a nuisance in the case of an FID measurement, does not pose any problem in the case of measurement by photo-ionization because the ionization potential of methane (12.6 eV) is less than the power of the lamp, which makes methane undetectable to PID. Photo-ionization just like the flame ionization technique, is particularly suitable for conducting measurements continuously. Both of these techniques give a global value of the species which one wishes to measure, but this value is given in an equivalent relatively to a reference compound, for example isobutylene in the case of the use of a detector by photo-ionization. On the other hand, photo-ionization measurement apparatuses are not designed for being capable of measuring hot gases (temperature limit of the order of 60° C.), since their main application lies in the measurement of pollutants, notably that of PAHs and VOCs in air. Accordingly, these apparatuses prove to be unsuitable for measuring tars in a hot medium, loaded with particles (requiring interposition of one or more filters) and with humidity, to which they are sensitive.

In the absence of knowing the composition of the tars as well as the response factors of different compounds, photo-ionization or flame ionization measurement no longer allows any continuous measurement of the total concentration of tars.

There exist other electronic methods which allow continuous monitoring of tars: these are detectors with electrochemical cells and sensors with semiconductors. An electrochemical cell consists of a membrane letting through the compounds to be analyzed by permeation; on the other side of the membrane is located a liquid electrolyte which, in the presence of the species to be detected, generates an oxidation-reduction reaction at the origin of a measurable electric current. This device is not suitable for a measurement in temperature, further the selectivity of the membrane is not compatible with the sampling of a large number of components, for which the physicochemical properties vary over a wide range of values. Sensors with semiconductors have similar limitations in terms of resistance to temperature, on the other hand a large number of pollutants may be measured with them. A significant limitation of this device also lies in the fast contamination of the sensitive layer of the semiconductor placed above the substrate. These so-called <<electronic>> methods allow the concentration of tars to be tracked continuously but a quantitative measurement of the totality of the tars present in a gas flow in temperature cannot be obtained;

a fourth family which groups the analysis methods based on coupling between at least two techniques, the first having a function for preparing the gas to be analyzed, for example a function for concentrating the chemical species to be quantified and present as traces, or a function for separating these same species, the latter providing the measurement function by means of a detector of the type of those described in families 1-3. In order to provide the separation function, the most currently used techniques are liquid phase or gas phase chromatography. To provide the detection function, the most currently used techniques in the case of measurement of tars are the flame ionization detector FID and the mass spectrometer MS. The latter is currently used for analyzing combustion gases from steel works. However the use of a mass spectrometer is not very suitable for conducting a quantitative measurement of tars present as traces and this even by carrying out many calibrations. Indeed, the low repeatability of measurements for the case of measurement of organic compounds of the tar type does not allow quantitative tracking of traces of tars. In the absence of a preliminary concentration step, chromatography coupled to a detector does not allow continuous measurements to be carried out for low detection thresholds (less than 1 mg/Nm$^3$). Moreover, the use of gas phase chromatography is not very suitable for measuring species for which the molar mass is relatively large (M>400 g/mol). The currently used methods for the concentration of traces are solid phase extraction (SPE), solid phase micro-extraction (SPME), and solid phase nano-extraction (SPNE). The SPME technique developed by Dr. Pawliszyn, in the 1990s consists in the absorption and/or adsorption of chemical species on a support covered with an absorbing and/or adsorbing species. This is a fibre of molten silica covered with a polymer, such as divinylbenzene (DVD), carboxene, polydimethyl siloxane (PDMS), etc. or a mixture of these compounds. This sampling step may pose a problem as to the representativity of the sampling because of the more or less selective character of the absorbent and/or adsorbent. This selectivity is related to many parameters which determine the physico-chemical affinity between a sampled molecule and the absorbent/adsorbent substance. In the case when the main mechanism which is applied is adsorption, there may exist adsorption competitions at the different species to be sampled. The selection of a fibre such as polydimethyl siloxane (PDMS) fibres allows this problem to be overcome since this substance behaves as a liquid (with regard to the sharing of the tars between the PDMS phase and the gas matrix) and thus applies an absorption mechanism which contrary to adsorption, does not cause any competition between the species to be sampled. In the absence of possible competitions between the sampled molecules, sampling is representative when there exists at equilibrium a proportionality relationship between the initial concentration of the compound (i) in the matrix to be sampled and the adsorbed/absorbed mass of the compound (i) on the fibre, provided that the sample volume should be sufficiently large. With these different concentration techniques, lower concentrations of pollutants may be detected. The temperature limit of SPME fibres is usually located between 240 and 340° C., the patent WO0017429 entitled <<solid phase micro extraction fibre structure and method of making>> reports a method with which PDMS fibres may be obtained with resistance to temperatures which may be above 360° C. Even in the presence of automatic sampling systems such as for example automatic sample changers, the duration of the measurement by means of a chromatograph coupled to a detector is not suitable for continuous measurement of traces of tars.

Patent EP0586012 proposes a device for measuring the content of certain hydrocarbons which may be present in tars (line 5 of page 2) which consists of taking samples with an adsorption device and having them pass through separation, extraction and measurement means which may comprise a chromatograph or a mass spectrometer. The method applied by this device requires the use of a solvent in order to elute the adsorbed tars on the adsorbent/absorbent solid used for the concentration step. With this device, it is not possible to conduct a continuous analysis of the tars and further a measurement of all types of tars because of the selectivity of the preparation.

A continuous measurement of the total concentration of tars in a gas can thus not be obtained by chromatography.

Thus, most methods for measuring tars are above all qualitative and discontinuous, so that they cannot meet an industrial need which is on-line and continuous monitoring of the concentration of tars.

Moreover, very frequently, an additional step for filtering and removing steam is required in order to limit the perturbations of the measurement on the one hand and possible degradations of the measurement material on the other hand. The same applies for the presence of oxygen.

None of the presented solutions is therefore able to meet the following requirements: a continuous, quantitative, total, and on-line measurement of traces of tars (detection threshold less than one mg/Nm$^3$).

None of the present devices is able to carry out a measurement of the total concentration of tars continuously with a measurement occurrence of the order of one minute.

Moreover, the presented devices do not measure the whole of the tars, whether they are in a solid phase or in the gas state.

The pursued goal is to carry out a quantitative and continuous measurement of the whole of the tars present in the solid phase or the gas state in a gas flow in temperature. Further, the measurement should be representative of the total tar content prevailing in a main conduit in which flows a synthesis gas under given temperature and pressure conditions.

GENERAL DESCRIPTION OF THE INVENTION

The aforementioned objects are achieved by the present invention. This is a device and a method for continuous measurement of the total concentration of tars in a gas, which may be tar traces.

By total concentration, is meant a concentration integrating the whole of the tars as defined above.

By trace tars, are meant tars for which the total concentration is of a few milligrams per normal cubic meter or less.

The present invention proposes a coupling of methods for measuring tars in a gas phase, one being discontinuous and a priori partial, the other being continuous but difficult to interpret as regards its sole raw data. This coupled device may be more or less sophisticated depending on the fineness of the sought information.

According to a general definition of the invention, the latter relates to a device for continuously measuring the tar concentration in a gas characterized in that it comprises a first measurement line and a second measurement line, the first measurement line being equipped with a first detector and the second measurement line being equipped with a second detector and means for extracting samples from the gas and means for separating components from the tars of the gas upstream from the second detector.

As this was already seen, the sensors for measuring the tar concentration do not generally allow continuous measurements, and those which allow this give results which are not quantitative and representative of the total tar concentration in a gas. To summarize, in the present invention, a first measurement line carries out a continuous measurement and a second measurement line performs samplings with which the results obtained by the first measurement line may be regularly calibrated, by calculating a global correction coefficient stemming from a law of mixtures.

The means for extracting gas samples comprise, in a preferred embodiment of the invention, a solid for absorbing or adsorbing reversibly tars, which may be in a preferred embodiment an SPME fibre or a set of such fibres. More preferably, PDMS fibre will be selected. A difficulty with the measurements is actually caused by the presence of humidity in the gas. These difficulties are solved in some of the preferred embodiments of the invention, since picking up samples by absorption or adsorption is hydrophobic. Thus, the sought effect of low sensitivity to water content of the picking-up of solid samples is achieved by using a PDMS fibre with a diameter of 100 μm since the mass of absorbed compounds on such a fibre varies by less than 10% when the humidity level varies from 0 to 100%. The means for extracting a gas sample then also comprise a sampling ampoule where gas samples dwell; the fibre is housed in a syringe passing through a plug of the ampoule and slides therein in order to extend into the ampoule while awaiting that the tars of the gas contained in the ampoule are deposited on it.

This kind of sampling device allows the tars even present as traces in the gas to be concentrated and thus allows more accurate detection.

The means for extracting gas samples may be associated with a chromatography column for separating the components from the mixture of tars and optionally a mass spectrometer for recognizing them. The components of the mixture of tars then arrive on the detector of the second measurement line and their individual concentrations are measured. A calibration of the results given by the detector of the first measurement line from the instant when this sample is taken, then becomes possible.

The detectors of both measurement lines are preferably homogeneous and consist in a preferred embodiment of the invention in photo-ionization detectors (PID), or optionally flame ionization detectors (FID). Instead of a photo-ionization detector (PID), a flame ionization detector (FID) may be preferred if the gas matrix is not capable of influencing the measurement by being consumed. The same applies to the detector 32 of the other measurement line B2, which should anyway be identical with the latter. It was seen that these detectors allow continuous measurements, so that they are particularly suitable for measuring very low concentrations of tars, i.e. as traces, in accordance with one of the main goals of the invention. These detectors should further be insensitive to gases capable of perturbing the measurement, (notably) to hydrogen, to carbon monoxide and to methane which may be present in the gas, and which are actually present in the synthesis gas from gasification of biomass. This problem was solved by selecting a particular ionization energy range with which ionization of these gases is avoided, preferentially comprised between 10 and 11 eV, and more preferentially 10.6 eV. The invention may therefore be advantageously applied to such gases.

In practice, preferably a processor for exploiting measurements will be made available, connected to the first detector and to the second detector in order to exploit their results and synchronize them by indicating the sample-taking instants with the required accuracy.

Another optional aspect of the invention consists in the presence of a generator of calibrated tar-containing atmospheres which is connected to the first measurement line and to the second measurement line. With this generator it is possible to carry out calibration of the apparatuses and to calculate different coefficients required for obtaining a quantitative measurement which will be representative, according to criteria which may be adapted depending on the fineness of the sought measurement, of the total concentration of tars present in the gas flow.

This generator of tar-containing atmospheres may comprise a tank of liquid tar and a device for a gas stream crossing the tank, and finally a device located at the inlet of the tank in order to divide the gas stream into bubbles in the tank: this device utilizes the liquid-gas equilibrium of the tars and carries away part of the contents of the reservoir into the gas stream also as a gas. The samplings, carried out on products which are physically comparable with those which will be subject to measurements, will normally be of good quality.

Another aspect of the invention is related to the temperature and pressure conditions of the gas. It is advantageous if the first line and the second line are provided with heat-insulated conduits in order to notably avoid condensations of tars. Further, the measurements depend on the temperature and on the pressure of the gases. Humidity also has an influence on the detectors of the measurement line, but its influence on the coefficients linking the results of both lines is small if the pressure and the temperature of the gas flow remain constant. Further, the water content remains stable enough in practice in most applications.

It is however desirable to provide the first measurement line with means for adjusting the temperature and pressure of the gases upstream from the detector, especially in the case of a photo-ionization detector, which is not designed for operating at a very high temperature. Temperature or pressure adjustments of a gas flow may therefore be necessary. Moreover, agreement between both measurement lines depends on coefficients which themselves depend on the measurement temperature, so that it may indicated to maintain the temperature of the gas flow at a constant value.

Also, the temperature, and especially the pressure of the gas flow, may be adjusted in the second measurement line, notably because absorption or adsorption of samples is easier at higher pressure. The second measurement line may then comprise an enclosure for conditioning the pressurized gas in front of the means for extracting samples.

An originality of the invention is the use of a PID or FID sensor for performing the continuous measurement of a gas for which the tar content has an unknown and variable composition, whereas such detectors which are known as suitable for giving a continuous measurement, are normally only used for measuring compounds having known compositions.

Another originality of the invention is the parallel use of two measurement lines connected to each other through a processing unit which synchronizes and utilizes them by deriving from one of them a calibration coefficient, here called a response coefficient, of the continuous detector in order to express the measurement of this detector and by periodically renewing this coefficient.

A still further originality of the invention is the use of a PID or FID detector for the second measurement line, which carries out discontinuous measurements, while such detectors are not preferred for such measurements because of their lesser accuracy; but their rapid measurements allow frequent samplings which may be directly used for the other detector. Therefore in the invention, two identical detectors will be used, i.e. which measure the same physical phenomenon (photo-ionization or flame ionization), without the identity of the detectors having to extend to all their details, of manufacture for example.

Still another originality of the invention is to obtain samples of tars at in a sufficiently concentrated condition in order to provide a satisfactory calibration even they are as traces.

Still another originality is the use of a calibration criterion based on only the predominant tars so as not to slow down the calibration of the detector continuously or make it impossible, to the cost of an accepted uncertainty of the measurement.

In correlation with the previous one, another originality of the invention is the verification of a consistency criterion between the continuous measurements of the detector and sequential measurements of the detector, so as to allow correction of the calibration if consistency is insufficient.

Finally with the invention, it is possible to perform measurements on gases comprised between 25° C. and 500° C. of temperature and 1 bar and 10 bars of pressure, notably.

Depending on the foregoing, another aspect of the invention is a method for continuous measurements of the total concentration of tars which may exist as traces, in a gas, characterized in that it comprises:

first continuous measurements of said total concentration at a first detector, which is a photo-ionization or flame ionization detector, periodic extractions of gas samples, every time followed by separation of the different species of tars present in said samples, measurement of concentrations of said species, and inference of a response coefficient of the first detector from the concentrations of said species.

and continuous estimations of the total concentration of tars by the measurements of the first detector and the response coefficient of the first detector.

It should be noted that <<species of tars >> will also be simply called <<tars >> in the following of this description.

The method advantageously comprises a selection of the species by only retaining predominant species in the gases for the sampling. Advantageously, a periodic estimation of the total concentration of tars by the second sensor is made, as well as a comparison of this periodic estimation with a simultaneous estimation derived from continuous estimations of the total concentration of tars. A failure of this comparison may then demand a complement to the retained selection of species.

BRIEF DESCRIPTION OF THE DRAWINGS

The invention will be better understood upon reading the detailed description which follows of embodiments on the invention provided as an illustration and by no means as a limitation, with reference to the appended drawings, wherein.

DETAILED DISCUSSION OF PARTICULAR EMBODIMENTS

Figure 1:
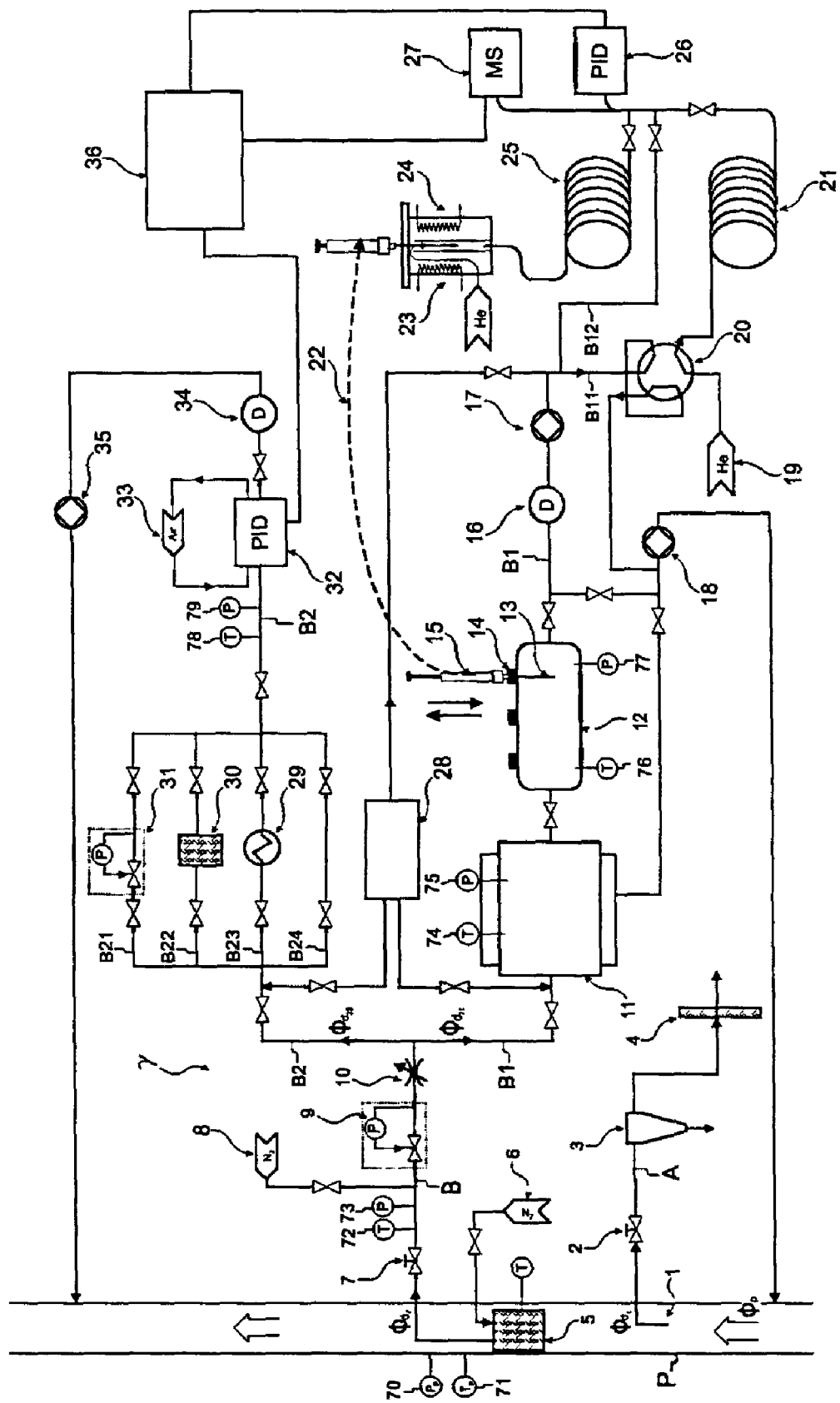
FIG. 1 schematically illustrates a device according to the invention, the goal of which is the continuous measurement of tars present in the gas or solid state in a gas flow in temperature.

First of all with reference to FIG. 1, a device dedicated to the measurement of tars present in the solid state and in the gas state is illustrated schematically.

The gas mixture to be analyzed flows inside a main conduit P in stainless steel, for example AISI 310 or AISI 316. Also alloys based on nickel and chromium (for example Inconel) are currently used as a constitutive material of conduits which may withstand temperatures of 1,200° C. and beyond and have the advantage of having a very small catalytic effect for the formation of coke, which allows the deposit of coke or soots to be limited on the internal surfaces of the ducts. Said conduit P comprises means 70 and 71 allowing continuous measurement of the pressure $P_p$ and the temperature $T_p$ which prevail inside it. The nature and composition of the gas mixture varies depending on the contemplated application. For example, in the case of a synthesis gas obtained by gasification of biomass or waste, the species present in majority are CO et $H_2$, both of these compounds form the gas matrix. To a lesser extent, gases are found such as $CO_2$, $CH_4$, $H_2O$ and various pollutants including tars. In the case when the synthesis gas would be intended for producing synthetic fuel, the gas flow upstream from the Fischer-Tropsch process is at a temperature of about 300° C. and at a pressure which may range up to 30 bars.

As illustrated in FIG. 1, a portion of the main flux $\phi_p$ is diverted towards two sampling devices and gives rise to secondary flows $\phi_{d1}$ and $\phi_{d2}$. Actually the global measurement system comprises two devices, the first of which is assigned to discontinuous measurement of the tars in the solid phase and the second to continuous measurement of the tars in the gas state. It is this second device for continuous measurement of the tars in the gas state which is the subject of the invention and which will be mainly described: the first device is optional and is a simple auxiliary intended to complete the measurement.

In order to limit the perturbation of the main flow $\phi_p$ and also in a concern for saving synthesis gas, the sample flow $\phi_d = \phi_{d1} + \phi_{d2}$ satisfies the following relationship:

$$\frac{\phi_d}{\phi_p} < 1\%$$

In the case when the whole of the tars present in the main flow $\phi_p$ would be in the gas phase (for example for temperatures above 350° C. and partial pressures of tars i less than the saturating vapor pressures), the first device would not required except for verifying the absence of solid tars. Beyond this temperature, the condensation of the tars in the aerosols present in the gas is strongly limited i.a. because of the minimization of the adsorption phenomenon of the organic compounds on the solid or liquid particles.

The first device, assigned to the measurement of tars in the solid phase, comprises an isokinetic sampling device 1 according to the ISO 9096 and/or ISO 2066 standards. The isokinetic sampling 1 is connected through metal stainless steel conduits A and a cut-off valve 2 on these conduits A to a particle sorting unit such as for example a cyclone 3 or a set of cyclones which perform the separation between the particles with a size larger than a few µm, notably coal or "char" particles, byproducts of pyrolysis of the biomass, and the particles with more modest size such as soots which originate from polycondensation of the tars. Said soots are then collected by impaction on a filtering medium 4 in order to be weighted in a second phase. The whole of the conduits of this device is heat-insulated and maintained at the temperature $T_p$ of the main conduit in order to avoid condensation of the tars present in the gas state in the main flow.

The second device, intended for continuous measurement of gas tars, consists of four large sub-assemblies which are:
 a system for sampling and conveying the gases (5, 6, 7, 8, 9 and 10);
 a calibration device (28, 19, 20 and 21);
 a first measurement line B1 (29, 30, 31, 32, 33, 34 and 35), dedicated to continuous measurement of the total tar content, given in equivalent relatively to a reference compound;
 a second measurement line B2 (11, 12, 13, 14, 15, 16, 17, 18, 22, 23, 24, 25, 26 and 27), which allows the measurement from the first measurement line to be recalibrated or validated or invalidated;
 and an assembly dedicated to data processing (36).

The system for sampling and conveying the gases (5, 6, 7, 8, 9 and 10) is located downstream from the isokinetic sampling system 1 in order not to perturb the latter.

The gas sampling and conveying system is heat-insulated and maintained at temperature $T_p$ in order to avoid generation of "cold areas" which would promote condensation of the tars. The question is also to convey the gas to be analyzed up to two measurement lines B1 and B2 under temperature and pressure conditions as close as possible to those prevailing in the main conduit P in order to avoid condensation and reactions of the tars. The question is therefore to have a measurement of the concentration of tars present in the gas state which is as representative as possible of that existing in the main conduit P. Maintaining the temperature of the conduits and of various other elements (7, 9 and 10) may be accomplished by means of an electric heating device or by circulation of hot nitrogen around said conduits and other units for conveying the gas to be analyzed.

The sampling system comprises a frit 5 which may be metal. The constitutive material of the frit should be cleverly selected in order to limit the catalytic effect leading to the formation of coke and therefore to destruction of tars; this for example may be a material formed on the basis of silicon carbide. The frit 5 may just as well and this in a non-limiting way be in quartz, ceramic or glass fibre. Said frit 5 is maintained in temperature by means of a heating device in order to avoid condensation of tar compounds notably promoted by the pressure loss which it induces. The frit 5 is used as a filter for the solid particles but allows a portion of the gas flow to flow in a sampling conduit B leading to the measurement lines B1 and B2. The sampling conduit B is heat-insulated and maintained at temperature $T_p$ of the flow, prevailing in the main conduit P.

A cut-off valve 7 placed downstream from the frit 5 allows the sampling conduit B to be isolated from the main conduit P.

The gas sampling and conveying system comprises means 72 and 73 with which the temperature and pressure inside the sampling conduit B may be measured.

A purge conduit 8 allows the whole of the measurement line B1 to be purged; the latter will be described later on.

An expansion valve 9 placed on the sampling conduit B allows the pressure in conduits B1 and B2 to be lowered and maintained constant.

A flow limiter 10 allows the flow $\phi_{d2}$ to be adjusted if need be.

The calibration device (28, 19, 20 and 21) will now be described with reference to FIGS. 1 and 2. The calibration device comprises:
 a tar atmosphere generator 28 which allows generation of a standard tar atmosphere in order to calibrate the measurement;
 a multi-way control valve 20 with its carrier gas supply system 19 and a column 21 of the capillary column type for gas chromatography. The multi-way control valve 20 is designed in order to inject the carrier gas 19 and the gas originating from the tar atmosphere generator 28 through a conduit B11 towards the column 21 and towards a photo-ionization detector 26 through a conduit B12 and vice versa by selection, in order to achieve the calibration described at the end of this description.

The tar atmosphere generator 28 will now be described with reference to FIG. 2. The generator 28 comprises:
 a tar supply system (45, 46, 47, 54, 55);
 a vapor generator by liquid-gas equilibrium (50, 57, 58, 60 and 61);

a sub-assembly for post-treatment of the generated atmospheres (41, 43, and 44);
a servo control system (42, 48, 51, 52, 53, 56 and 59) for controlling the amount of vaporized tars.

The supply system comprises tanks (45 and 47) storing as a liquid the tars which are conveyed towards a thermostatted bath 57 by means of peristaltic pumps (54 and 55). The different tanks are supplied through a supply orifice 46 or 106.

The vapor generator comprises a pressurized nitrogen supply 61 provided with an anti-return valve 60, both positioned at the bottom of the thermostatted bath 57. A means for measuring pressure 90 is added. Said thermostatted bath 57 comprises a frit 58 positioned in its bottom. The frit 58 has the role of generating fine nitrogen bubbles which will flow through the liquid mixture of tars while carrying away a portion of the latter. The thereby formed vapors will escape through an outlet orifice 50.

The post-treatment sub-assembly has the goal of performing i.a. a dilution of the generated tar vapors in order to obtain atmospheres with low tar content. For this purpose, a pressurized nitrogen supply 41 is connected to a mixer 43 in which a mixing of the tar vapors and of the inert gas occurs. An exchanger 44 is positioned downstream from said mixer 43 in order to change the temperature of the generated atmosphere if need be. The different conduits in which the tar atmosphere flows are heat-insulated and maintained in temperature. Said conduits are also provided with means 97, 98 and 99 dedicated to measurement of temperature and of pressure. A steam supply 63, positioned upstream from the mixer 43 may be used in order to change the water content of the generated tar atmospheres. This adjustment may be carried out by opening a micrometric valve 94 located on a conduit connecting it to the mixer 43. The supplies 41 and 63 are each provided with a pressure measurement means 95 or 96 and a flowmeter 42 or 64.

The servo control system comprises a data processing unit 59 of the microprocessor type which provides temperature control of the thermostatted bath 57 by means of a heating device and of a sensor, not shown here. Maintaining the level of liquid tars present in the bath 57 is ensured by tracking the altitude of a magnetic float 11 with a position detector. Regulation of the position of the magnetic float 51 is accomplished via control of the flow rates of tars as measured by the flowmeters 53 and 56 each positioned on a conduit leading from a respective tank 45 or 47 of tars to the bath 57. Each of these conduits is further provided with a discharge pump 54 or 55 and a cut-off valve 92 or 93. Finally, a return conduit 48 starting from the bottom of the bath 57 and provided with a discharge pump 62 is capable of pouring back the tar content of the bath 57 into either one of the tanks 45 or 47 through a distribution valve 95 or of discharging it through another distribution valve 91. The bath 57 is provided with a temperature measurement device 107.

Figure 2:
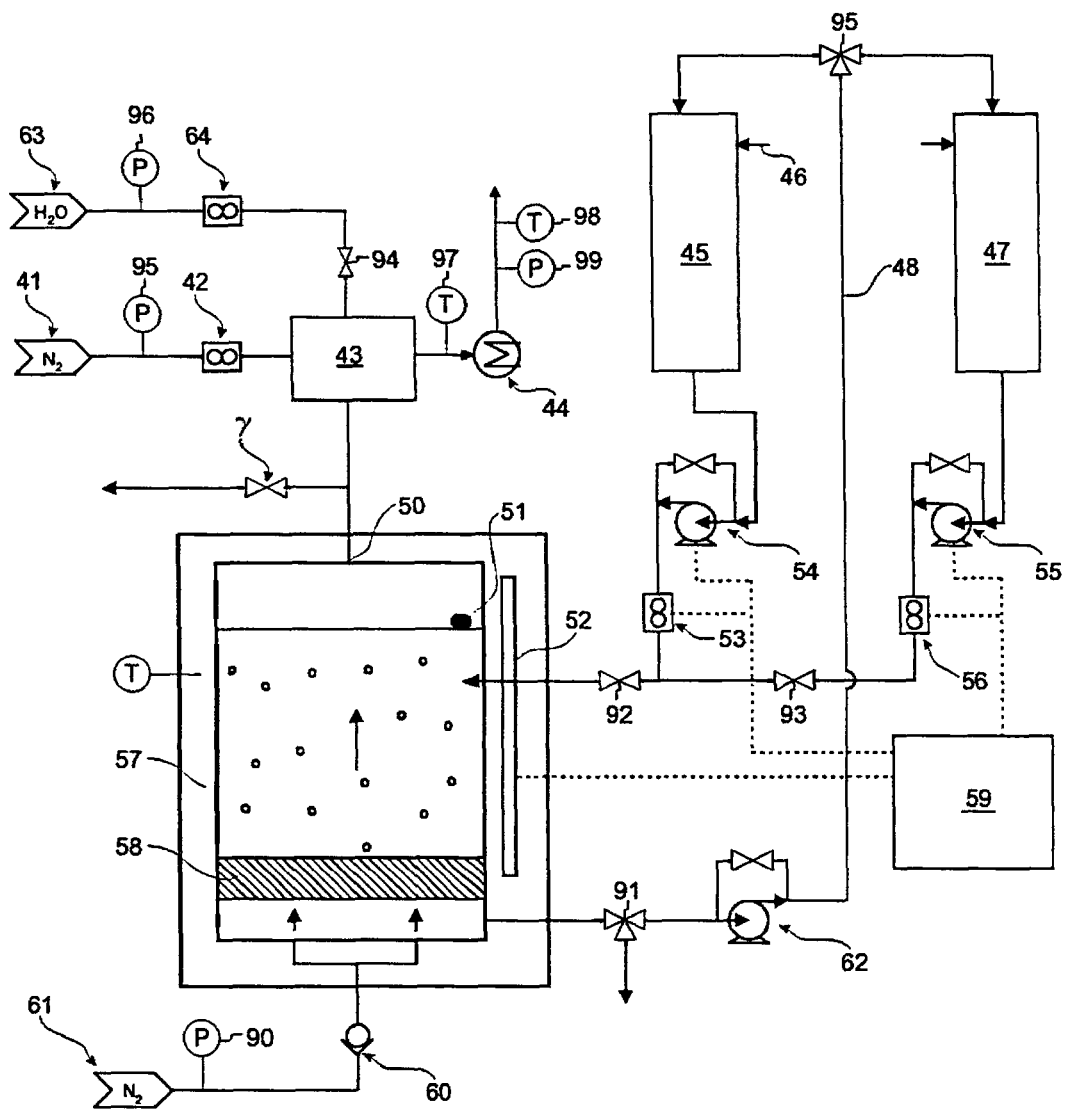
FIG. 2 is a device for generating vapors of tars with which the different detectors as well as the SPME fibre may i.a. be calibrated.

The device shown in FIG. 2 is an exemplary embodiment of a tar atmosphere generator 28 which is by no means limiting. This device is particularly suitable for tars which are in the liquid state under standard conditions of temperature and pressure (SCTP). In the case of tar in the solid state, a device applying a fixed bed of solid tars crossed by a flow of carrier gas may be contemplated.

The measurement line B1 will now be described with reference to FIG. 1.

The measurement line B1 comprises:
4 treatment routes B21, B22, B23 and B24 positioned in parallel, for the gas to be analyzed. The route B21 comprises an expansion valve 31 which allows the pressure to be lowered if need be. The route B22 comprises a filtering medium 30 with which one or more molecules may be adsorbed/absorbed preferentially, this may be water for example. The route B23 comprises a heat exchanger 29 with which the temperature of the gas to be analyzed may be lowered or on the contrary increased. The route B24, as for it, is unoccupied and heat-insulated;
a PID (Photo Ionization Detector) detector 32 which was modified in order to withstand pressure and temperature;
measurement means (78, 79 and 34) with which the temperature, pressure and flow rate may be determined continuously. Information on the flow rate is given by a volumetric counter 34. The conduit B2 ends up by returning to the main duct P for pouring back the sampled gas therein. A discharge pump 35 is responsible for establishing the sampled gas flow.

Upstream from the photo-ionization detector 32, the heat exchanger 29 and an adsorbent and/or absorbent medium 30 are implanted in order to be able to adjust the temperature of the analysis if need be and selectively adsorb/absorb species, the discrimination of which in the global signal may be relevant if necessary. The UV lamp of the PID 32 is selected so that the provided ionization energy cannot ionize molecules other than tars. The ionization energy provided by the lamp should be less than the first ionization energies of compounds other than tars, i.e. less than 14 eV and more advisably less than that of oxygen (12.1 eV) so that a possible presence of air is not a source of perturbation for the measurement. The PID 32 may advisably be adapted to levels of temperature strength (for example from 0 to 200° C.) and of pressure strength (for example from 1 to 10 bars) in order to provide a significant signal of the actual content of gas tars present in the flow to be characterized. To do this, particular constructive arrangements are taken close to the PID detector (32):
a first arrangement consists of positioning an optical UV-transparent interface; as mentioned in patent WO1994027141 between the gas and the ampoule. The idea is to protect the lamp against deposits of carbonaceous compounds which have the effect of limiting the life time and efficiency of the lamp. In the case of our application, the question is also to limit the heat transfers from the gas to the ampoule in order to minimize thermal stresses inherent to the measurement of a hot gas. The question is also to protect the ampoule from the pressure to the extent that the ampoule is depressurized; a pressure measurement is capable of providing better sensitivity of the apparatus since for a given volume of the ionization chamber, there are more ionized molecules;
another arrangement consists of designing the optical interface so as to be mobile in order to allow replacement of the latter;
another arrangement consists of using in the ionization chamber materials which withstand temperatures of the order of 400° C., or even above; these may be ceramics for the walls and quartz for the optical interface for example. Another PID detector 26 which will be mentioned later on may receive the same fittings. An air-injection system 33 controls a circuit for sweeping air through the PID detector 32 in order to periodically clean the deposits having built up in the ionization chamber and on the optical interface.

The measurement line B2 will now be described with reference to FIG. 1. The measurement line B2 comprises:
a conditioning enclosure 11 with which the temperature and the pressure of the gas to be analyzed may be adjusted;

a sampling system comprising a thermostatted sampling ampoule 12, one or more septa 14, an SPME fibre 13 with its injection system which comprises a syringe 15 and an automatic sample changer 22;

a volumetric counter 16;

a volumetric pump 17;

a column 25 for gas chromatography of the capillary column type;

an injector 24 for an SPME fibre 13;

a set of synchronized detectors which comprise a PID 26 (photo-ionization detector) and a mass spectrometer 27.

With the conditioning enclosure 11, it is possible to adjust the pressure and the temperature of the gas to be sampled. Indeed, the temperature and the pressure and both parameters which have to be optimized in order to then allow optimum extraction of the tars at the sampling ampoule 12. Temperature 74 and pressure 75 measurement means equip the confinement enclosure 11.

The sampling system comprises a sampling ampoule 12 which is thermostatted, and also equipped with temperature 76 and pressure 77 measurement means. The internal surface of the ampoule is treated so as to limit adsorption phenomena (polished stainless steel for example). The ampoule is equipped with one or more septa 14 (sealed passage plugs) allowing one or more SPME (Solid Phase Micro Extraction) sampling syringes 15 to introduce one or more fibres adapted to the selected temperature and pressure conditions in the thermostatted ampoule 12. The tars will be gradually adsorbed/absorbed on the SPME fibre until sorption equilibrium is reached. At equilibrium, the mass of adsorbed/absorbed compounds is maximum. There then exists a proportionality relationship between the concentration on the SPME fibre of species i, $C^\infty_{fibre}(i)$, and that of the species i in the ampoule 12, $C^\infty_{ampoule}(i)$ Both of these quantities are related by the constant $K(i)$, called the partition coefficient of the fibre between the compound i present in the gas matrix to be sampled and the SPME fibre. The quantity $K(i)$ is defined as being the ratio of these two concentrations:

$$K(i) = C^\infty_{fibre}(i)/C^\infty_{ampoule}(i)$$

These partition coefficients $K(i)$ depend on the compound i and on temperature. These coefficients are assumed to be known for each tar i and for the range of temperatures at which the sampling is performed. On a given temperature domain, there exist simple linear laws giving log $K(i)$ as a function of $1/T$:

$$K(i) = Ko \cdot \exp((-\Delta H/R) \cdot (1/T - 1/To))$$

It should be noted that the volume $V_{ampoule}$ of the sampling ampoule 12 should be sufficiently large so that the total concentration of tars in the gas phase is not significantly modified; the relative variation induced by the extraction of the tars on the SPME fibre(s) put into contact with the gas phase to be characterized, should not exceed 5% ideally in order not to significantly modify the sorption equilibrium. Indeed, Gorecki and Pawliszyn "The effect of sample volume on quantitative analysis by solid phase microextraction. Part 2. Experimental verification", Gorecki T., Khaled A., Pawliszyn J., (1998), 123, 2819-2824 have shown that the sampling volume may affect results of quantitative analysis if $100 \cdot K(i) \cdot V_{fibre}$ is larger than $V_{ampoule}$.

The sampling ampoule 12 may be put into relationship with the vacuum pump in order to impose a pressure suitable for extracting tars on the retained SPME 13 fibre. The imposed temperature is comprised between the maximum admissible temperature of the SPME fibre 13 (depending on the nature of the latter) and the sampling temperature allowing optimized adsorption, i.e. sufficiently rapid (ideally less than one minute) and guaranteeing sufficient sensitivity (i.e. allowing the sought detection threshold of the sampling method to be attained). Indeed, the higher the sampling temperature, the more rapid is the reaching of the equilibrium conditions and the lower the amount of adsorbed compounds.

With the automatic sample changer 22 sampling by SPME may be automated. It allows both injections of a SPME fibre into the thermostatted ampoule 12 and into the injector 24 of the chromatograph 25.

The chromatograph 25 performs separation of the different compounds depending on their retention time in the capillary column.

Figure 3:
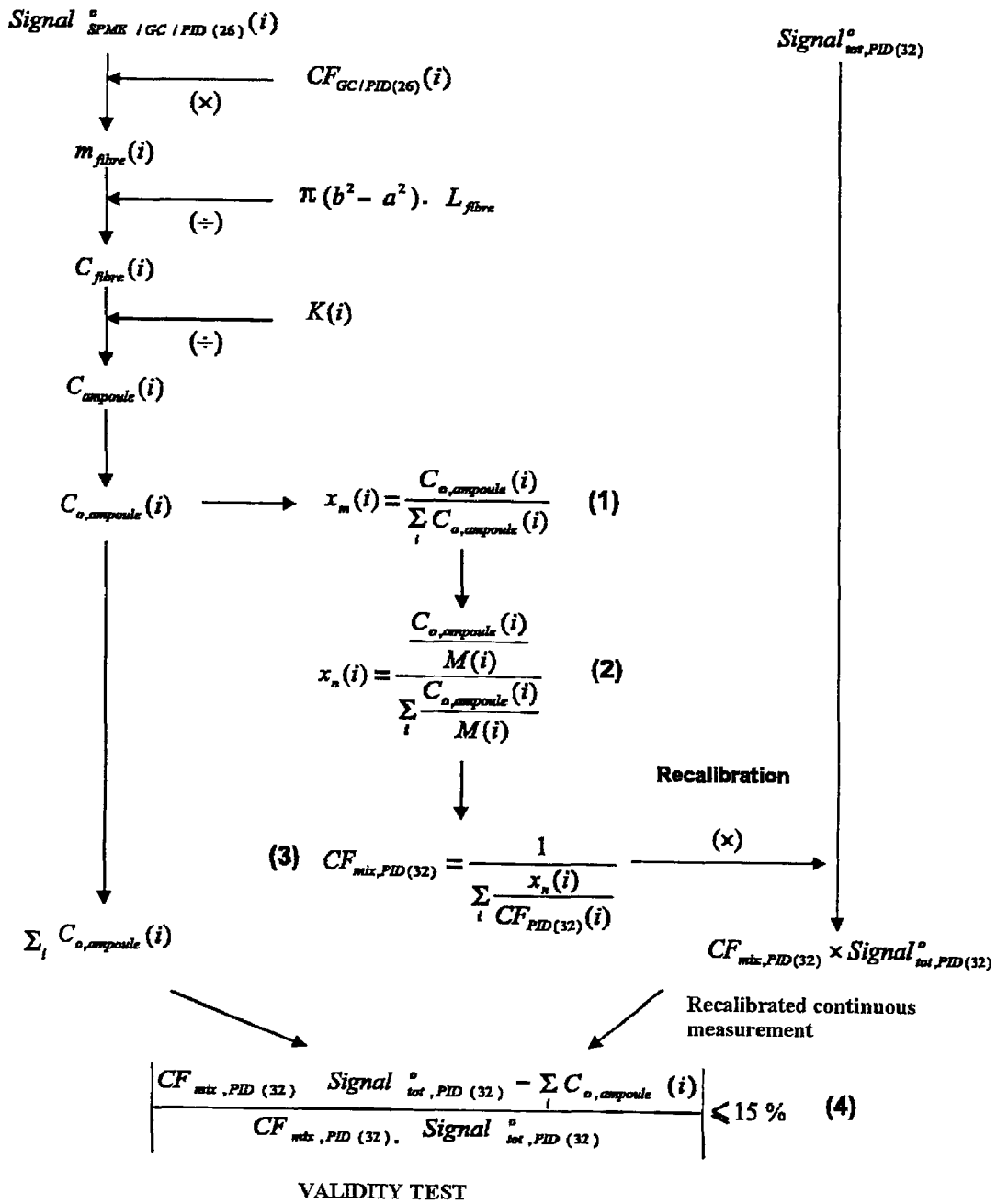
FIG. 3 illustrates a block diagram of the different calculation steps leading to the determination of the total concentration of tars.

The spectrometer 27 is located after the column 25, it allows identification of the tars extracted from SPME fibre 13. With it, it is possible to return a posteriori to the composition of tars present in the gas mixture before sampling with the relevant SPME fibre 13 from measurements given by the PID 26 and from formulae which will be described hereafter (FIG. 3).

The detector PID 26 synchronized with the mass spectrometer 27 thus allows quantification of the species of tars identified by the mass spectrometer 27. The ionization energy of the lamp of the PID should be less than the values of the ionization energies of the molecules of permanent gases (CO, $H_2$, $CO_2$ and $CH_4$) forming the gas matrix of the flow to be characterized.

The information processing sub-assembly will now be described, which consists of a computer unit 36 with which data provided by the tar detectors, the mass spectrometer 27 and both PIDs 26 and 32, may be acquired and processed. This device notably applies an algorithm (FIG. 3). The computer unit 32 has the purpose of:

identifying the species of the tars separated at the outlet of the chromatograph 21 or 25 by means of the mass spectrometer 27. This identification is made on the basis of a comparison between the decomposition spectra given by the mass spectrometer 27 and those contained in a database. The identification tool integrated to the information processing device is a standard element for comparing signals notably taking into account possible interferences (superpositions) between the different spectra;

associating with each of the compounds identified by decrypting the mass spectra, a quantitative measurement provided by its response to the PID 26. The latter is synchronized with the mass spectrometer 27;

associating with the response of the PID detector 26 (by preliminary calibration) a concentration of each of the compounds identified earlier in the gas flow of the line B1. To do this, the correspondence between the concentration on the SPME fibre 13 of each compound i and that in the sampling ampoule 12 will have been evaluated beforehand by using partition coefficients $K(_i)$ (determined for a given fibre, temperature and pressure) between the gas matrix and the given SPME fibre 13;

comparing the sum of the signals given by the PID 26 by taking into account the SPME/GC/MS·PID correspondence with the global signal given by the detector PID 32. With the global function of the information processing device 36 it is possible to continuously a "real" quantitative measurement of the whole of the tars present in the gas state in a flow in temperature and pressure.

The operation of the gas sampling and conveying system (5, 6, 7, 8, and 10) will now be described with reference to FIG. 1.

During normal operation, a portion of the main flow $\phi_p$ is sampled at the isokinetic sampling device 1. The cut-out valve 2 is open and lets through the sampled flow which crosses the cyclone 3 or carries out a separation between the coal (or <<char>>) particles, byproducts of the pyrolysis of the carbon-rich biomass, and the condensed tars. The tars are then conveyed in conduits maintained at temperature $T_p$ towards a filtering medium 4, where by impaction, the already condensed tars are trapped. The temperature of the main conduit $T_p$ above 300° C. limits condensation of the gas tars on the filtering medium 4. Downstream from the isokinetic sampling device 1, a portion of the main flow $\phi_p$ is deviated into a secondary flow $\phi_{d2}$. The particles are trapped by the frit 5 maintained at temperature $T_p$. The intermittent operation of a pressurized nitrogen supply 6 towards the frit 5 avoids fouling of the latter. The cut-out valve 7 allows the measurement device to be isolated from the main conduit P. The expansion valve 9 is positioned upstream from the measurement lines B1 and B2 in order to lower the pressure to a level which is compatible with the latter.

The operation of the measurement line 1 will now be described with reference to FIG. 1.

During normal operation, a portion of the gas flow sampled at the main conduit is conveyed towards the measurement line B1.

In the case of a static SPME extraction, the conditioning enclosure 11 is depressurized, as well as the sampling ampoule 12 by a volumetric pump 18. The valves 109 and 110 are then closed so as to isolate the sampling ampoule 12 from the remainder of the circuit. A valve 108 is then opened so that the enclosure 11 is filled by the deviated flow $\phi_{d21}$. During this time, the automatic sample changer 22 will place one or more syringes 15 each containing an SPME fibre 13 retractable through the different sampling septa 14 of the sampling ampoule 12. Indeed, one may be lead to position several identical or different fibres in the ampoule so as to optimize the extraction of the whole of the compounds. With the enclosure 11, it is possible to perform temperature and pressure conditioning of the sampled gas. Temperature and pressure are parameters which have to be optimized as this will be described later on. The valve 108 is then closed and the valve 109 opened to that the gas contained in the enclosure 11 fills the sampling ampoule 12. The tars as well as other compounds will be absorbed on the SPME fibres 13 with a concentration of tars on a small volume, very useful for the subsequent measurement. After a time t equal to 5 minutes for example, the automatic sample changer 22 will place the syringe 15 on the injector 24. The absorbed compounds will be thermally desorbed in the injector 24 in a relatively short time (<30 s) and will be carried away through the column 25 by a carrier gas 19. The use of an injector without any leak rate (splitless) allows the totality of the desorbed compounds to be injected through the column 25 and thereby increase the sensitivity of the whole of the measurement line B1. An SPME fibre 13 may be reused about a hundred times or even more so. Regeneration of the fibres is performed under a flow of nitrogen in an enclosure thermostatted to 250° C. for 15 min. A carrier gas such as helium originating from an injector 23 carries away the different compounds desorbed in the chromatograph where they will be retained for a more or less long period of time in the column 25 according to their affinity relatively to the stationary phase of the column 25 of the gas chromatograph. For a given chromatograph and operating conditions, the retention time is characteristic of one or more species which will be identified by mass spectrometry 27 as a well determined compound i. In parallel, information on the amount of the compound i is given by the signal delivered by the PID 26 Signal$_{SPME/GC/PID(26)}^{o}$(i). The signals delivered by the detectors 26 and 27 which are synchronized will be analyzed and processed by the processor 36 in order to carry out calculations from which a representative measurement of the total concentration of tars prevailing in the main conduit will result. The different calculations will be presented later on. In the presence of several SPME fibres 13, it is advantageous if the adsorption on one of them is simultaneous with the chromatographic measurement on the tars on another one of them in order to reduce the sampling intervals by performing the chromatography in a concurrent operation time.

The measurements on the fibres 13 may be conducted before reaching the sorption equilibrium in order to accelerate the sampling measurements to the cost of a loss of sensitivity; moreover, the use of fibres as nanotubes or nanostructures may be recommended in order to increase the mass of adsorbed tars, to increase the resistance of the fibre to temperature and to enhance desorption at the injector 24 for a better quality of the observed chromatographic peaks.

The operation of the measurement line 2 will now be described with reference to FIG. 1.

During normal operation, a portion of the gas flow sampled at the main conduit is conveyed towards the measurement line B2. Depending on the pressure and/or the temperature in the main conduit and the pressure and temperature strength limit of the PID 32, the secondary flow $\phi_{d22}$ will be conveyed towards the B21 or B23 line where the expansion valve 31 and the heat exchanger 29 are positioned respectively. The filtering medium 30 may be used for preferentially adsorbing/absorbing one or more components for which discrimination in the global signal will be relevant. The flow $\phi_{d22}$ is then conveyed right up to PID 32 which carries out a continuous measurement or at the very least calculates an average value for a time interval less than one minute. The signal delivered by the PID 32 Signal$_{tot,PID(32)}^{o}$ is recalibrated every pT (T sampling period, p being a non-zero natural integer) by a correction coefficient CF$_{mix,PID(32)}$ which is considered as constant for a duration equal to the sampling period T and the calculation of which will be explained later on.

The different calibration operations required for obtaining a quantitative measurement will now be described. Indeed, for the present invention, it is necessary to proceed with four types of calibration in the order stated below so as to determine the following response coefficients:

the response coefficients CF$_{PID(32)}$(i) of the PID 32 for tars i, which are the species of tars comprising the mixture to be studied;
the response coefficients CF$_{PID(26)}$(i) of the PID 26 for tars i;
the response coefficients CF$_{GC/PID(26)}$(i) for the assembly {GC+PID 26} for tars i;
the partition coefficients K(i) of tars i for an SPME fibre and given temperature and pressure conditions.

Before being able to determine the response coefficients associated with the detectors PID 26 and 32, it is necessary to calibrate beforehand the signal from the latter relatively to a reference compound which may for example be isobutylene. As the response of the PID detectors is linear, at least two measurement points of the PID detectors are required. They are determined from both atmospheres with known isobutylene concentrations (for example 10 ppb$_v$ and 1,000 ppb$_v$).

For a same amount of tar i to be measured, the response of the signal of the detector, here in this case the detector PID 26 or 32, varies depending on the detected tar i. Indeed, this signal notably depends on the possibility of the tar i of causing the detector to react and therefore on its capability of being ionized by the PID detector. This capability is itself function of the first ionization potential, of the nature of the molecule and of the atomic bonds which make it up. It is therefore necessary in order to be able to compare each signal induced by different compounds, to proceed with calibration by which the expected response of the PID detector may be estimated (the signal of mass spectrometer often being more variable over time and less reproducible than the one provided by the detector PID) for a known amount of introduced tar i.

The calibration of the detectors PID 26 and 32 is performed by using standard atmospheres with increasing concentration of tar i, generated by the tar atmosphere generator 28. As the concentration of tars of said atmospheres is known, the question is to read the response of the PID detector (26 or 32) for each concentration and to then carry out a linear regression in order to correctly estimate the response coefficient $CF_{PID(26)}(i)$ or $CF_{PID(32)}(i)$ defined as follows:

$$CF_{PID}(i) = \frac{C_{generator\_tars}(i)}{Signal^0_{PID}(i)}$$

wherein $Signal_{PID(26)}^0(i)$ represents the signal from the PID 26 or 32 given in isobutylene equivalent. The unit of the response coefficient $CF_{PID}(i)$ is mg·Nm$^{-3}$/ppb$_v$. The coefficients $CF_{PID}(i)$ depend:

on the power of the lamp (for example 10.6 eV);
and on the water content which cannot affect the value of the response coefficient $CF_{PID}(i)$ by more than 30% when the relative humidity of the gas to be analyzed varies from 0 to 100%.

If the response coefficient of the PID $CF_{PID}(i)$ is small, then the PID has a large measurement sensitivity for the tar i and conversely if $CF_{PID}(i)$ is large, then the sensitivity of the PID relatively to the tar i is low. It should be noted that the response coefficients $CF_{PID(26)}(i)$ and $CF_{PID(32)}(i)$ for a same tar i may be different insofar that the temperature and pressure conditions under which the measurements are carried out may differ from one detector PID to the other.

The procedure for calibrating the {GC/PID(26)} assembly will now be described, which may be accomplished in several ways. A first way consists of directly injecting via line B11 and the multi-way valve 20 an atmosphere with a known tar concentration into the column 21 and to read the signal provided by the detector PID 26 $Signal_{GC/PID(26)}^0(i)$ given for example in isobutylene equivalent. The question is then to calculate for each tar i by a linear regression (a minimum of 2 measurement points) the following response coefficient:

$$CF_{GC/PID(26)}(i) = \frac{m_{injected}(i)}{Signal^0_{GC/PID(26)}(i)}$$

Wherein $Signal_{GC/PID(26)}^0(i)$ represents the signal of the sub-assembly {GC+PID(26)} given in isobutylene equivalent. The unit of the coefficient $CF_{GC/PID(26)}(i)$ is mg/ppb$_v$.

Another way for calibrating the assembly {GC/PID(26)} is to introduce a micro-syringe containing a known mass $m_{injected}(i)$ of tar i into the injector 24 and to then read the signal delivered by the PID detector 26 and this for different masses $m_{injected}(i)$. The response coefficient $CF_{GC/PID(26)}(i)$ is then determined by linear regression for each tar i.

It should be noted that it is possible, in order to save time for calibration, to inject an atmosphere of n tars i, the composition and total concentration of which are known in order to proceed with simultaneous determination of several response coefficients by using the law of the following mixtures:

$$CF_{mix,PID(26)} = \frac{1}{\sum_{i=1}^{n} \frac{x_m(i)}{CF_{PID(26)}(i)}}$$

The calibration of the SPME fibre consists of determining the partition coefficients K(i) between the SPME fibre 13 and each tar i present in the gas matrix to be sampled. K(i), an adimensional quantity, is defined at equilibrium by the following formula:

$$K(i) = \frac{C^\infty_{fibre}(i)}{C^\infty_{ampoule}(i)}$$

wherein $C_{fibre}^\infty(i)$ represents the concentration of tar i on the SPME fibre 13 at equilibrium and $C_{ampoule}^\infty(i)$ represents the concentration of the tar i in the sampling ampoule 12 at equilibrium.

There exist different ways for determining the K(i). A first method consists of using the response coefficients $CF_{GC/PID(26)}(i)$ as determined beforehand so that starting from the introduction of an atmosphere of n tars, for which the concentrations $C_{ampoule}^\infty(i)$ generated by the device 28 for generating tar atmospheres are known, it is possible to calculate at equilibrium the concentration of the tar i on the SPME fibre $C_{fibre}^\infty(i)$, expressed in mg·Nm$^{-3}$, from the following formula:

$$C^\infty_{fibre}(i) = \frac{m^\infty_{fibre}(i)}{V_{fibre}} = \frac{10^3 \times m^\infty_{fibre}(i)}{\pi \times (b^2 - a^2)}$$

A second method mentioned in the document entitled <<Estimation of Air/Coating Distribution Coefficients for Solid Phase Microextraction Using Retention Indexes from Linear Temperature-Programmed Capillary Gas Chromatography. Application to the Sampling and Analysis of Petroleum Hydrocarbons in Air >>, Anal. Chem. 1997, Martos, Pawliszyn, consists of determining the partition coefficients K(i) of an SPME fibre in PDMS for a given class of species, for example n-alkanes, from chromatographic retention indexes LTPRI (Linear Temperature-Programmed Retention Index) by means of a linearity relationship. The use of this formula requires that the K(i) of different compounds have been determined beforehand for a given SPME fibre in order to infer the linearity law which will allow the calculation of the other K(i) of the compounds belonging to the same family. This method has the advantage of strongly reducing the time required for experimental determination of the set of K(i) for a given group of species. Partition coefficient values K(i) of different tars i for a 100 μm PDMS SPME fibre at a temperature of 80° C. at a pressure of 1 bar are given in Table I.

TABLE I

VALUES OF THE PARTITION COEFFICIENT OF DIFFERENT TARS I FOR A 100 μM PDMS SPME FIBRE AT A TEMPERATURE OF 80° C. AND AT A PRESSURE OF 1 BAR.

| Tars | K (i) |
|---|---|
| Indene | 3711 |
| Methyl phenol | 11014 |
| Dimethylphenol | 17739 |
| Naphthalene | 10833 |
| Dodecane | 11834 |
| Tridecene | 22450 |
| Methylnaphthalene | 24961 |
| Tridecane | 23655 |
| Tetradecene | 45216 |
| Acenaphthylene | 62627 |
| Acenaphthene | 77695 |
| Pentadecene | 81264 |
| Pentadecane | 91502 |
| Fluorene | 139635 |

The different operations for optimizing the different parameters will now be described.

First of all, one must proceed with optimizing the parameters of the gas chromatograph comprising capillary columns 25 and 21 which are strictly identical. The stationary phase is selected to be identical with that of the SPME fibres 13. The injection temperature in the injector 24 is selected to be slightly below the limiting temperature strength temperature of the SPME fibre 13 in order to have as fast as possible desorption in order to have chromatographic peaks of optimum quality. The question is then to optimize the heating program to be imposed to the oven of the capillary columns 21 and 25 as well as the carrier gas flow rate 19. In order to check that the chromatograph is not limiting for our application, an atmosphere with a known concentration $C_{generator\_tars}(i)$ of tars i is directly injected at the PID detector 26 and the signal $Signal_{PID(26)}^o(i)$, expressed in $ppb_v$ is read. In the same way, the same atmosphere is injected into the capillary column 21 by the injection loop of the multi-way valve 20 and the signal $Signal_{GC/PID(26)}^o(i)$ is read at the PID 26. The multi-way valve 20 is in the condition illustrated in FIG. 3B, the carrier gas 19 having purged the sampling loop. The different parameters then have to be optimized so as to verify the following inequality:

$$\sum_{i=1}^{n} \frac{Signal^o_{GC/PID(26)}(i) - Signal^o_{PID(26)}(i)}{Signal^o_{PID(26)}(i)} \leq 10\%$$

Once the different parameters of the chromatograph have been optimized, the question is to optimize the sampling conditions by SPME. The optimization steps for the SPME sampling are identical with those of the chromatograph. The question is to verify the following relationship:

$$\frac{Signal^o_{SPME/GC/PID(26)}(i) - Signal^o_{GC/PID(26)}(i)}{Signal^o_{GC/PID(26)}(i)} \leq 10\%$$

The parameters on which it is possible to act are:
the extraction temperature;
the pressure;
the selection of the fibre (nature of the adsorbent/absorbent and dimensions of the fibre).

Figure 4:
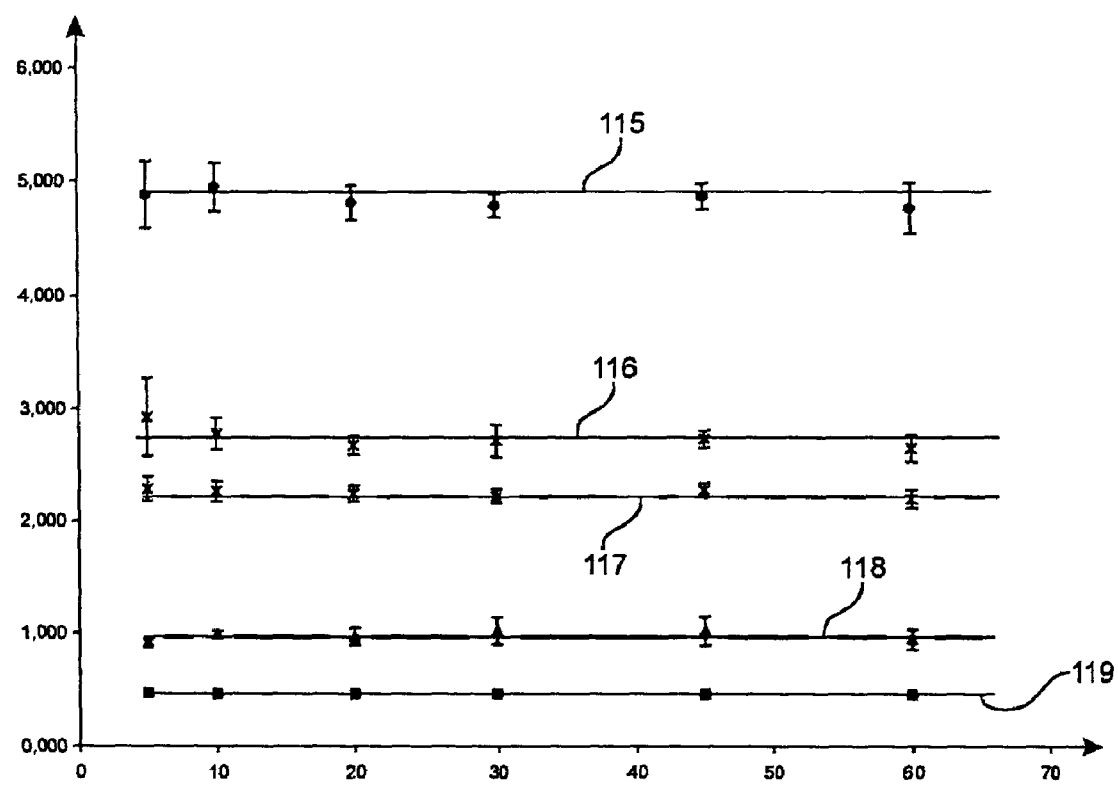
FIG. 4 is a graph showing the absorption kinetics of several tars on a PDMS fibre with a diameter of 100 μm at the temperature of 80° C. and at a pressure of one bar.
Figure 5:
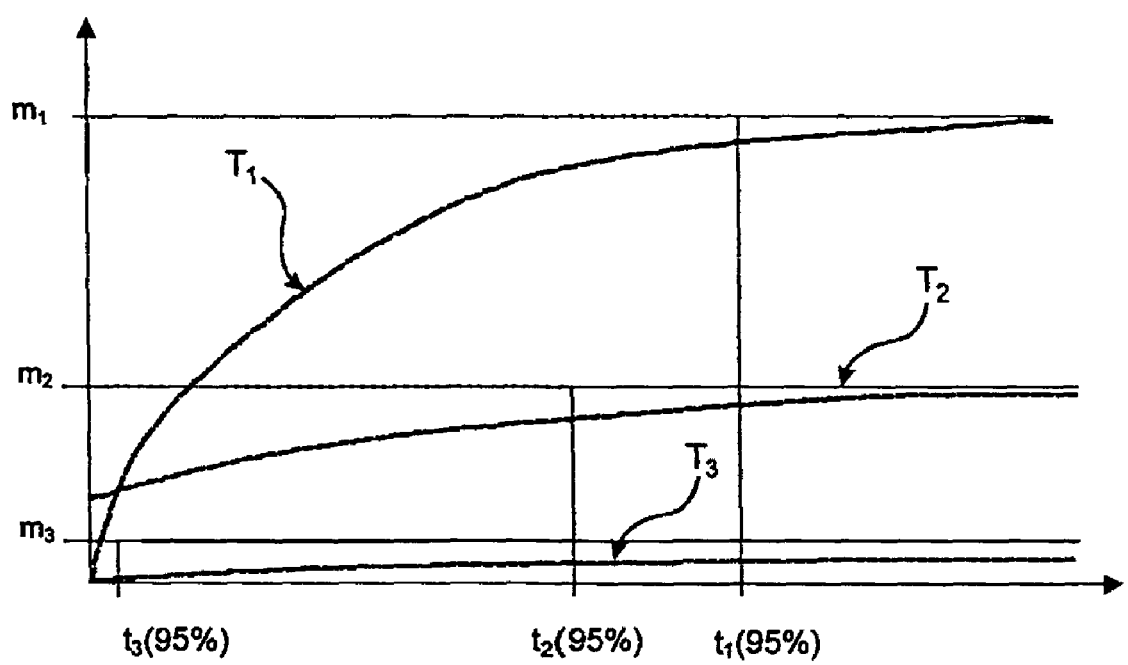
FIG. 5 illustrates a graph showing the change in the extracted mass of tars i on an SPME fibre versus the exposure time of the latter and this for different temperatures.

The operating conditions for SPME sampling which are the pressure and temperature are two parameters which should be optimized in order to have an extraction of the tars present in the gas state which is sufficient in terms of amount and sufficiently fast, i.e. the time for reaching equilibrium should be less than 5 min. The temperature is determined so as to have a good compromise between good sensitivity of the measurement (depends on the mass of absorbed compounds at equilibrium $m^\infty_{fibre}$) and a relatively short sampling time (less than 5 min). In FIG. 5, which indicates masses extracted from the fibre in ordinates and exposure times of the fibre in abscissae; the extraction at temperature $T_2$ ($T_3 > T_2 > T_1$) is a compromise between the strong induced sensitivity (large value of $m_1$) at the extraction temperature $T_1$ on the one hand but a relatively long time for reaching equilibrium $t_{1(95\%)}$, and the rapidity of the extraction conducted at temperature $T_3$ ($t_{3(95\%)}$ relatively low) but a low response level induced at the extraction temperature $T_3$ on the other hand. At the temperature of 80° C., equilibrium sorption is attained for most tars i after 5 min (FIG. 4). The exposure time appears in minutes and in abscissae and the extracted mass in nanograms in ordinates, curves 115, 116, 117, 118 and 119 are respectively valid for fluorene, acetonaphthylene, acetanophthalene, 2-methylnaphthalene and naphthalene. In the case of the invention, pressurized SPME extraction is recommended since it is particularly of interest for measuring traces of tars. Indeed for a given volume, the amount of adsorbed tars on SPME fibre 13 increases with pressure in a certain given range. However, the value of the pressure is limited by the condensation phenomenon of tars which occurs when the partial pressure of a tar i becomes higher than its saturating vapor pressure. A measurement in pressure therefore allows sufficient SPME extraction sensitivity and thus the temperature may be increased, which will prevent certain tars for condensing and thereby reduces the time for reaching equilibrium. Moreover, the gas to be characterized is pressurized in the main conduit P, so that it is possible to approach actual measurement conditions.

It should be emphasized that the sampling of the invention has the particularity of being dual and of thereby imposing observance of a compromise, and first a partition of the tars between the fibre 13 and the ampoule 12: the fibre 13 is used for separate sampling of the different species of tars, and the contents of the ampoule 12 for overall sampling of the gas. Even if condensation of the tars in FIG. 13 is requested, it should not excessively deplete the content of the ampoule 12. This is also for obtaining satisfactory overall sampling so that condensations on the ampoule 12 may be avoided, which gives preference to relatively high temperatures and fibres 13 which withstand such temperatures.

For a pressure of one bar and for a PDMS 100 μm fibre, the maximum temperature in the sampling ampoule 12 allowing a detection threshold to be reached, close to 0.1 mg·Nm⁻³ for most species, by chromatography coupled with a flame ionization detector, is 80° C. (FIG. 5). The detection threshold for naphthalene at a pressure of 80° C. and at the pressure of one bar is 80 μg·m⁻³. The previous detection threshold was determined by assuming the following criterion:

$$\frac{Signal}{Noise} \geq 100$$

This criterion was retained because the criterion usually considered for determining detection thresholds (signal-tonoise ratio of 2) does not allow quantitative measurement in the sense that the maximum committed error may be 50%.

The data processing system 36 comprises a processor and one or more databases dedicated i.a. to recognition of spectra. In the case when the values of the response coefficients explained earlier are not available, it is necessary to the determine the tars i, for which the response coefficients should be calculated as a priority. For this, measurements are carried out at the line B2 and, by means of the PID detector 26 synchronized with the mass spectrometer 27, the tar for which the signal $\text{Signal}_{SPME/GC/PID(26)}^{o}(i)$ is maximum, is located. This tar is defined as being tar 1. In the same way, an ordered sequence of n tars is defined such that the sum of their signals is equal to 90% (this threshold is not mandatory) of the sum of the total signals delivered by the PID detector 26. Next, determination of the whole of the response coefficients for the whole of these tars is sought. These response coefficients allow the signal to be actually quantified by calculating, as this will be seen later on, the concentration of these n tars before SPME sampling. With this, it is possible to create an initial database which will be enriched during the various measurements by identifying new tars for which the contribution to the total concentration is sufficient (<1% for example). The data processing and calibration subassembly gives real autonomy which allows enrichment of the database.

The calculation algorithm applied by the data processing system 36 will now be described with reference to FIG. 4.

Every $\Delta t$, n signals $\text{Signal}_{SPME/GC/PID(26)}^{o}(i)$ are emitted by the assembly {SPME/GC/PID}. Each signal $\text{Signal}_{SPME/GC/PID(26)}^{o}(i)$ is multiplied by the response coefficient of the assembly {GC/PID} $CF_{GC/PID(26)}(i)$, which gives the value of the tar mass i absorbed on the SPME fibre 13 at equilibrium $m_{fibre}^{\infty}(i)$. The later is proportional to the concentration $C_{fibre}^{\infty}(i)$ of the tar i at the surface of the fibre at equilibrium (b and a are the outer radius and inner radius of the absorbent portion of the fibre, and $L_{fibre}$ is its length). The question is then to divide the quantity $C_{fibre}^{\infty}(i)$ expressing the concentration of the tar i on the fibre by the partition coefficient K(i) between the SPME fibre and the tar i present in the gas matrix to be sampled in order to obtain the concentration $C_{ampoule}^{\infty}(i)$ of the tar i present in the sampling ampoule 12 at the moment of equilibrium; this concentration is not very different (<5%) from the initial concentration $C_{o,ampoule}(i)$ of the tar i present in the sampling ampoule 12 upon filling the latter. The set of the $C_{o,ampoule}(i)$ will be summed in order to calculate the mass fractions $x_m(i)$ and the molar fractions $x_n(i)$ of each tar i (cf. equations (1) and (2) of FIG. 3) which allow the quantity of interest to be calculated, i.e. the global correction coefficient of the PID 32 $CF_{mix,PID(32)}$ which also involves the different response coefficients $CF_{PID(32)}(i)$ of the tars i to the PID detector 32. The response coefficient of the mixture $CF_{mix,PID(32)}$ is determined from the following law of mixtures (cf. equation (3) of FIG. 3) and is expressed in mg·Nm$^{-3}$/ppb$_v$:

$$CF_{mix,PID(32)} = \frac{1}{\sum_{i=1}^{n} \frac{x_m(i)}{CF_{PID(32)}(i)}}$$

The continuous signal $\text{Signal}_{tot,PID(32)}^{o}$ is multiplied by the coefficient $CF_{mix,PID(32)}$, the latter is considered as constant during $\Delta t$. The obtained value $\text{Signal}_{tot,PID(32)}^{o} \times CF_{mix,PID(32)}$ is a continuous value of the total tar content which is representative of the one prevailing in the main conduit, provided that the following inequality (4) (FIG. 3) is verified:

$$\left| \frac{CF_{mix,PID(32)} \times \text{Signal}_{tot,PID(32)}^{o} - \sum_{i} C_{o,ampoule}(i)}{CF_{mix,PID(32)} \times \text{Signal}_{tot,PID(32)}^{o}} \right| \leq 15\%$$

The inequality above may be verified at variable intervals depending on the necessity of the measurement.

One should dwell at length on these steps of the method. The periodic sampling performed by the detector 26 does not normally affect the totality of the species of the tars i making up the mixture, since their number is often very large and that some may be unknown or may escape specific detection, if for example their concentration is too low. The calculation of the response coefficient $CF_{mix}$, PID (32) is actually performed by means of the predominant tars in the mixture and present in the database, provided that they are assumed to sufficiently represent the actual composition of the mixture, which justifies the 90% threshold proposed before, although other values may be selected. The omission of certain tars making up the mixture introduces an additional uncertainty on the calculation of the response coefficient, where however it is accepted in exchange for the possibility of rapidly sampling the gas and obtaining the coefficient at a sufficient rate in order to allow continuous sampling by the detector 32 of the first line of measurement. The accepted 15% uncertainty threshold is of course itself arbitrary. If it is not observed, a new calculation of the response coefficient $CF_{mix}$, PID (32) may be repeated by involving a larger number of tars entering the composition of the mixture. Other reasons for which this inequality is not verified, may be the following:

the temperature and/or the pressure at the PID detector 32 is unsuitable;
 some compounds other than tars significantly contribute to the response at the PID detector 32;
 some tars i are not detectable by the PID detector.

It may then be recommended to change the operating conditions of the process, notably by adjusting the temperature or the pressure, or by using a filtering medium. The flow may be switched via the B21, B22, B23 and B24 routes for this.

The response coefficients determined by the measurement line B1 give information on the limitations of the different materials and parameters used. Further, with the measurement line B1 it is possible to verify that the whole of the detected tars by the mass spectrometer 27 are actually measurable with the PID detector 26. In the same way, the compounds significantly contributing to the response of the PID detector 26 and which are not tars, are identified by the synchronized indication of the mass spectrometer 27. This is information on the limitation of the invention which may lead to the use of a filtering medium 30 in order to absorb these compounds which would have a non-negligible contribution in the global signal provided by the PID detector 32. Another means would consist of carrying out a comparative measurement at the measurement line B2 by replacing the filtering medium 30 by a catalytic bed allowing cracking of the tars to be performed continuously. Next, the question would be of adding a PID detector in parallel on the PID detector 32 in order to compare the signal from the cracked flow with that of the non-cracked flow.

Exemplary Embodiment

The different components of the tar measurement device are dimensioned depending on the volume flow rate of gas $\phi_p$ flowing in the main conduit and on the pressure and temperature conditions, respectively $P_p$ and $T_p$ prevailing in the latter.

A dimensioning example is provided below, by considering a volume flow rate of 100 Nm³/h for a diameter of the main conduit of 1½ inches. The pressure and the temperature prevailing inside the latter are 10 bars and 400° C. respectively. The deviated flow $\phi_{d2}$ is about 0.7 Nm³/h, the secondary flows $\phi_{d21}$ and $\phi_{d22}$ are 0.35 Nm³/h and 0.35 Nm³/h, respectively.

Targeted measurement range: from 0.1 to 50 mg·Nm⁻³
Material of the filtering medium 4: glass fibre
Porosity of the filtering medium 4: 1 μm
Dimensions of the filtering medium 4: disc with a diameter of 4 cm
Outer dimensions of the frit 5: 5 mm×5 mm
Pressure loss of the frit 5 under no load conditions: <0.1 bar
Porosity of the frit 5: 0.1 to 2 μm
Efficiency of the frit 5: 99.9% for a particle diameter above 2 μm.
Maintained temperature of the frit 5: 400° C.
Maintained temperature of the ducts and of the other elements upstream from the measurement lines B1 and B2: 400° C.
Diameter of the connecting conduits: ⅛ inch or 3 mm;
Sampled gas flow rate $\phi_{d2}$: 0.7 Nm³/h
Temperature in the conditioning enclosure 11: 20-1000° C.
Pressure at the conditioning enclosure 11: 1-10 bars
Material of the sampling ampoule 12: polished stainless steel
Volume of the sampling ampoule 12: 20 L
Pressure inside the sampling ampoule 12: 1-10 bars
Type of SPME fibre 13 used: PDMS
Thickness of the SPME fibre 13: 100 μm
Length of the SPME fibre 13: 1 cm
Sampling temperature at the thermostatted ampoule 12: 80-120° C.
Sampling time: 5 min
Diameter of the filtering medium 30: 5 cm
Height of the filtering medium 30: 10 cm
Power of the bulb of the PIDs 26 and 32: 10.6 eV
Injector type 24: conventional liner
Injection temperature 24: 270° C.
Injection duration 24: <30 s
Diameter of the capillary columns 21 and 25: 0.2 mm
Length of the capillary columns 21 and 25: 10 m
Material of the stationary phase of the columns 21 and 25: PDMS
Carrier gas 23 used: He
Duration of the chromatographic measurement: 5 min
Mass spectrometer type: quadripolar
Temperature at the exchanger 29: 105-400° C.
Purge pressure 6: 6 bars
Volumetric counter 16 and 34: 0-1 m³·h⁻¹

The invention claimed is:

1. A device for continuous measurement of the total concentration of tars, which may even be in the form of traces, in a gas characterized in that it comprises:
a first line for continuous measurement of the total amount of tars, by means of a photo-ionization or flame-ionization detector (32),
a second line for sequential measurement of the total amount of tars successively including means for extracting and concentrating the tars present in the gas (12, 13), means for separating different species of tars concentrated previously (25), means for identifying the different species of tars separated previously (27) and a detector identical with the one of the first measurement line (26),
a generator of calibrated tar atmospheres connected to the first measurement line and to the second measurement line,
means for processing the measurements (36) from the first detector (32) and from the second detector (26), capable of comparing the data for each of the detectors (26, 32) in order to indicate the total amount of tars measured by means of the first detector from measurements made with the second detector.

2. The measurement device according to claim 1, characterized in that the means for extracting and concentrating gas samples comprise a solid with reversible absorption or adsorption.

3. The measurement device according to claim 2, characterized in that the means for extracting and concentrating samples of the gas comprise a sampling ampoule, a syringe passing through a plug of the ampoule, and in that the solid is a fibre sliding in the syringe.

4. The measurement device according to claim 3, characterized in that the fibre is in PDMS (polydimethylsiloxane) or in a carbonaceous compound (of the carbon nanotube or graphitic structure type).

5. The measurement device according to claim 1, characterized in that the first detector and the second detector are photo-ionization detectors.

6. The measurement device according to claim 5, characterized in that the photo-ionization detectors are adjusted to a value comprised between 10 and 11 eV, preferentially to 10.6 eV.

7. The measurement device according to claim 1, characterized in that the means for separating the different species of tars concentrated previously are a chromatograph.

8. The measurement device according to claim 1, characterized in that the means for identifying the different species of tars separated previously are a mass spectrometer.

9. The measurement device according to claim 1, characterized in that the measurement lines are heat-insulated and maintained at constant temperature.

10. The measurement device according to claim 1, characterized in that the generator of tar atmospheres comprises a tank of liquid tars, a device with a gas stream passing through the tank, and a device at the inlet of the tank in order to divide the gas stream into bubbles in the tank.

11. The measurement device according to claim 1, characterized in that the first measurement line comprises means for adjusting temperature.

12. The measurement device according to claim 1, characterized in that the second measurement line comprises an enclosure (11) for conditioning the pressurized gas before the means for extracting samples.

13. A method for continuous measurement of the total concentration of tars, which may be even in the form of traces, in a gas, characterized in that it comprises:
first means for continuous measurement of said total concentration have a first detector (32) which is a photo-ionization or flame-ionization detector,
periodic extractions of samples of gas, every time followed by separation of different species of tars present in said samples, by measurement of the concentrations of said species by a second detector (26), and by inference of a response coefficient of the first detector (32) from the concentrations of said species, and continuous estimations of the total concentration of tars by the measurements of the first detector and the response coefficient of the first detector.

14. The method for continuous measurement of the total concentration of tars in a gas according to claim 13, characterized in that the response coefficient of the first detector is the reciprocal of the sum of the ratios of the concentration and of a particular response coefficient of the first detector, for each of said species.

15. The method for continuous measurement of the total concentration of tars in a gas according to claim 13, characterized in that it comprises a selection of the species, only retaining predominant species in the gas.

16. The method for continuous measurement of the total concentration of tars in a gas according to claim 15, characterized in that the retained species give a global signal on the second detector having a relationship with a total signal of the sample which is above a threshold.

17. The method for continuous measurement of the total concentration of tars in a gas according to claim 15, characterized in that it comprises, for each of the samples, a periodic estimation of the total concentration of tars by the second detector (26) and a comparison of said periodic estimation with a simultaneous estimation inferred from continuous estimations of the total concentration of tars.

18. The method for continuous measurement of the total concentration of tars in a gas according to claim 17, characterized in that it comprises a complement of the selection of retained species if a relative deviation between the periodic estimation and the simultaneous estimation is above a threshold.

19. The method for continuous measurement of the total concentration of tars in a gas according to claim 17, characterized in that it comprises a modification of the measurement conditions by the first detector if a relative deviation between the periodic estimation and the simultaneous estimation is above a threshold, the measurement conditions including temperature and pressure.

20. The method for continuous measurement of the total concentration of tars in a gas according to claim 17, characterized in that it comprises a modification of the measurement conditions by the first detector if a relative deviation between the periodic estimation and the simultaneous estimation is above a threshold, the measurement conditions including filtering of the gas.

21. The method for continuous measurement of the total concentration of tars in a gas according to claim 13, characterized in that the gas is at a temperature comprised between 25° C. and 500° C.

22. The method for continuous measurement of the total concentration of tars in a gas according to claim 13, characterized in that the gas is at a pressure comprised between atmospheric pressure and 10 bars.

* * * * *